(12) United States Patent
Largent

(10) Patent No.: US 6,312,424 B1
(45) Date of Patent: *Nov. 6, 2001

(54) METHOD OF VISION CORRECTION

(75) Inventor: James R. Largent, Santa Ana, CA (US)

(73) Assignee: Allergan, Waco, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 809 days.

(21) Appl. No.: 08/506,794

(22) Filed: Jul. 25, 1995

(51) Int. Cl.⁷ ..................................... A61F 9/01
(52) U.S. Cl. .................. 606/5; 606/10; 606/13; 128/898
(58) Field of Search ................. 606/2, 3–18; 128/898

(56) References Cited

U.S. PATENT DOCUMENTS

| 4,665,913 | 5/1987 | L'Esperance, Jr. . |
| 4,729,372 | 3/1988 | L'Esperance, Jr. . |
| 4,798,204 | 1/1989 | L'Esperance, Jr. . |
| 4,842,782 | 6/1989 | Portney et al. . |
| 4,856,513 | 8/1989 | Muller . |
| 4,941,093 | 7/1990 | Marshal et al. . |
| 4,994,058 | 2/1991 | Raven et al. . |
| 5,225,858 | 7/1993 | Portney . |
| 5,270,744 | 12/1993 | Portney . |
| 5,533,997 | * 7/1996 | Ruiz ......................................... 606/5 |

FOREIGN PATENT DOCUMENTS

| 0372127 | 6/1990 | (EP) . |
| 9325166 | 12/1993 | (WO) . |

OTHER PUBLICATIONS

Excimer Laser Surgery of the Cornea by Stephen L. Troekel, M.D. Sep. 1983 American Journal of Ophthalmology 96:710–715.

* cited by examiner

Primary Examiner—David M. Shay
(74) Attorney, Agent, or Firm—Stout, Uxa, Buyan & Mullins, LLP; Frank J. Uxa

(57) ABSTRACT

A method of vision correction comprising shaping first and second regions of a cornea to provide the first region with a first vision correction power and the second region with a second vision correction power which is different from the first vision correction power to enhance vision at first and second distances, respectively.

11 Claims, 1 Drawing Sheet

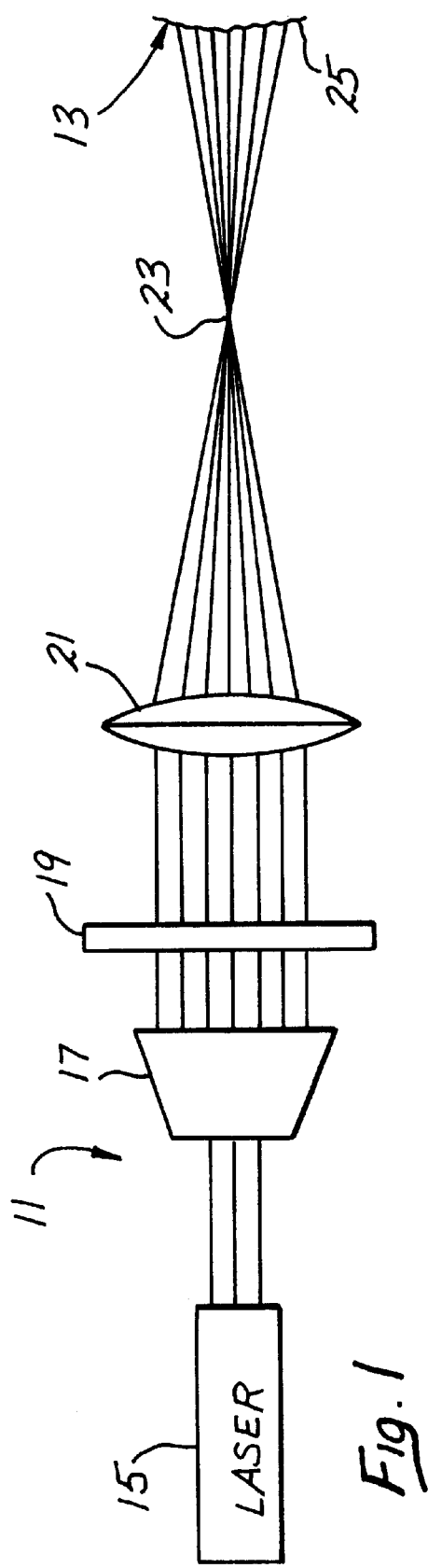
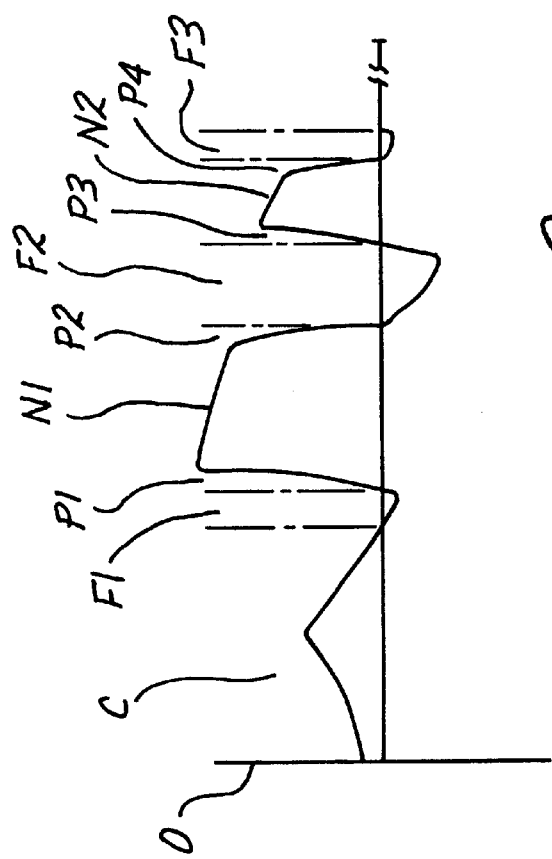

METHOD OF VISION CORRECTION

FIELD OF THE INVENTION

This invention relates to vision correction and more particularly to vision correction by shaping of the cornea.

BACKGROUND OF THE INVENTION

As is well known, vision correction is often obtained through the use of ophthalmic lenses, such as eye glasses and/or contact lenses. It is also known to employ corneal inlays, corneal onlays and intraocular lenses.

Another technique for vision correction is to modify the cornea, and this can be done, for example, through a radial keratotomy procedure. It is also known to shape the cornea utilizing a laser and to correct for nearsightedness, farsightedness or astigmatism.

It is not uncommon, however, for a patient to require correction for both near and far distances, and some patients also need correction for intermediate distances. It is also desirable at least in some instances to provide a patient with progressive vision correction powers. Although this can be accomplished thorough the use of ophthalmic lenses, so far as I am aware, multifocal correction and progressive correction through cornea shaping are not taught in the prior art.

SUMMARY OF THE INVENTION

This invention provides a method of vision correction which achieves multifocal and/or progressive vision correction through shaping of the cornea thereby enabling these corrections to be obtained without the need for an ophthalmic lens. The shaping of the cornea alters the configuration of the anterior surface of the cornea thereby changing its refraction. This cornea shaping technique can be utilized for patients having their natural lens or an intraocular lens.

The method of vision correction may include shaping first and second regions of the anterior surface of a cornea to provide the first region with a surface configuration which provides a first vision correction power and to provide the second region with a surface configuration which provides a second vision correction power which is different from the first vision correction power to enhance vision at first and second different distances, respectively. For example, the distances may be near and far distances to thereby provide a bifocal effect. Of course, the cornea shaping may be carried out to achieve trifocal correction or any other desired number of steps of vision correction.

An important feature of the invention is that the cornea may be shaped to provide progressive vision correction powers. For example, the step of shaping may include shaping a third region of the cornea between the first and second regions to provide a surface configuration which provides the progressive vision correction powers with the progressive vision correction powers including vision correction powers which are between the first and second vision correction powers.

The specific configuration of the power curve across the cornea can be tailored to suit the needs of the patient and particular design considerations. However, the preferred method includes shaping a fourth region of the cornea to provide a surface configuration which provides progressive vision correction powers which include progressive vision correction powers which are between the first and second vision correction powers. The second region is between the third region and the fourth region.

Likewise, the particular configuration of the regions which are shaped can differ widely. Preferably, however, each of the shaped regions is annular with the annular regions being in appropriate circumscribing relationship.

It also may be desirable to shape a central region of the cornea. In one preferred arrangement, the central region of the cornea is shaped to provide a vision correction power intermediate the first and second vision correction powers. Preferably the vision correction power of the central region includes an intermediate vision correction power.

It is conceivable that some time after the regions of the cornea are appropriately shaped to provide the desired vision correction that these regions will lose their shape and desired vision correction due to, for example, growth of the cornea. If this should occur, the method of this invention, and in particular the shaping steps of the method may be carried out again on the cornea of the patient to restore the desired configuration to thereby reestablish the desired vision correction. In addition, the same patient may require or desire further shaping of the cornea at some later date if, for example, the natural lens of the patient loses more accommodation.

Although the shaping of the cornea may be carried out in any suitable way, it is currently preferred to shape the cornea utilizing laser energy. Although this can be accomplished by scanning a laser beam across the cornea, it is preferred to utilize a mask which appropriately modulates the laser energy so the laser energy can shape the regions of the cornea to provide the desired vision correction powers.

According to one technique, laser energy is directed to a mask to provide a modulated laser beam having different energy levels at different locations across the modulated laser beam. The laser beam is then directed to the cornea to ablate the cornea to different degrees to provide the cornea with progressive vision correction powers and/or bifocal or trifocal powers. The different energy levels of the modulated laser beam enable the laser beam to accomplish differential ablation of the cornea to achieve the desired shape of the cornea. In order to provide the different energy levels, the mask may have variable or differential transmissivity or reflectivity to the laser energy provided by the laser. The mask may provide the modulated laser beam with appropriate annular zones which are capable of ablating annular regions of the cornea to achieve the desired cornea shaping effect.

The invention together with additional features and advantages thereof may best be understood by reference to the following description taken in connection with the accompanying illustrative drawings.

BRIEF DESCRIPTION OF THE DRAWINGS

FIG. 1 is a schematic illustration of one form of apparatus which can be used to carry out the vision correction method of this invention.

FIG. 2 is a schematic plan view showing one arrangement of vision correction powers which can be provided by shaping the cornea using the system of FIG. 1.

FIG. 3 is a plot of vision correction power versus distance from the center of the cornea for another preferred cornea shape.

DESCRIPTION OF THE PREFERRED EMBODIMENT

FIG. 1 shows a system 11 of the type which can be used to carry out the vision correction method of this invention to shape a cornea 13 of a human patient. The system 11 is much like the system shown and described in common assignees U.S. Pat. No. 4,842,782, and the disclosure of that patent is incorporated by reference herein. Generally, the system 11 comprises a laser 15 which directs laser energy toward a beam expander 17 which expands the cross section of the laser beam. The laser 15 is preferably an excimer laser of the type which can safely be used for delicate human tissue such as the cornea.

The laser energy from the beam expander 17 is directed toward a mask 19 which modulates the laser energy and provides a modulated laser beam having different energy levels at different locations across the modulated laser beam. The modulated laser beam from the mask 19 is directed toward a positive lens 21 having focal point 23. The lens 21, which in this embodiment, is a biconvex lens images the mask on the anterior surface 25 of the cornea 13. For this purpose, the patient's head is positioned accurately with respect to the system 11 and is held against movement with respect to the system 11 utilizing conventional techniques.

The modulated laser beam is therefore directed to the cornea 13 where it ablates the anterior surface 25 of the cornea to different degrees to alter the refraction of the cornea to provide the cornea with multifocal vision correction powers. The nature of the vision correction powers, i.e. the vision correction powers that are created at each location of the cornea is a function of the characteristics of the mask 19. Various different kinds of masks can be used to appropriately modulate the laser energy, and in that regard, the mask 19 may be erodible to different degrees at different locations along the mask or have different transmissivity or reflectivity to the laser energy at different locations over the surface of the mask. In the embodiment illustrated, the mask 19 has different transmissivity to laser energy at different locations on the mask.

The vision correction power of a refractive element, such as the cornea, is a function of the curvature of the surface of the refractive element. This is explained, for example, in Portney U.S. Pat. Nos. 5,270,744 and 5,225,858 both of which are incorporated by reference herein. In any event, the zones of the mask 19 which are the most transmissive to laser energy provide a stronger laser beam portion which ablates more of the cornea at the corresponding region. Conversely, a zone of the mask 19 which is of lesser transmissivity to the laser energy provides a relatively weak laser beam portion which is capable of a lesser degree of ablation of the corresponding region of the cornea. Thus, by selecting the transmissivity to the laser energy at each zone of the mask, the cornea 13, and in particular the anterior surface 25 of the cornea, can be shaped curved or configured as desired. This enables the curvature of the cornea to be changed at different regions of the cornea to achieve the desired multifocal effect, and this may include progressive vision correction powers.

FIG. 2 illustrates one example of the refractive power that may be placed on the anterior surface 25 of the cornea. Thus, in FIG. 2 there is a central region C of the cornea which preferably has an intermediate vision correction power. If desired, the power in the central region may be progressive. The central region is circumscribed by coaxial annular regions. Thus, the annular region F provides far vision correction powers, the annular region P1 provides progressive vision correction powers, the annular region N provides near vision correction powers and the annular region P2 provides progressive vision correction powers. If desired, the regions F and N may also include progressive vision correction powers, but their primary purpose is to achieve far and near correction, respectively.

Each of the regions P1 and P2 includes progressive vision correction powers which are between or intermediate the far and near vision correction powers of the regions F and N, and preferably all of the progressive vision correction powers of the regions P1 and P2 are intermediate the far vision correction powers of the region F and the near vision correction powers of the region N. In addition, the progressive vision correction powers of the region P1 include progressive vision correction powers which increase in a radial outward direction. Conversely, the progressive vision correction powers of the region P2 include progressive vision correction powers which decrease in a radial outward direction. Of course, if the regions F and N were reversed in FIG. 2, then the progressive vision correction powers of the regions P1 and P2 would also reverse such that the vision correction powers of the region P1 would decrease in a radial outward direction and the vision corrections powers of the region P2 would increase in a radial outward direction.

FIG. 3 illustrates another example of the refractive power that may be placed on the cornea. In this regard, FIG. 3 shows a plot of the power of the cornea versus distance from the optical axis or center of the cornea. The power curve of FIG. 3 is very similar to the power curve shown in FIG. 11 of Portney U.S. Pat. No. 5,225,858.

Shaping the anterior surface 25 of the cornea 13 to achieve the power curve of FIG. 3 requires that the cornea have a central zone C in which the power increases slightly in a radial outward direction from the optical axis O and then decreases toward the periphery of the central region. As with the embodiment of FIG. 2, the central zone C is circumscribed by a number of annular regions, and these include in radial outward order a far region F1, a progressive region P1, a near region N1, a progressive region P2, a far region F2, a progressive region P3, a near region N2, a progressive region P4, and a far region F3. It should be noted that the progressive regions P1 and P3 are of increasing vision correction power in a radial outward direction whereas the progressive regions P2 and P4 are of decreasing vision correction power in a radial outward direction. Also, the far regions F1, F2 and F3 and the near regions N1 and N2 all include some progressive powers. By appropriately tailoring the transmissive characteristics of the mask 19, the anterior surface 25 of the cornea can be configured to provide refractive vision correction powers in accordance with either of FIGS. 2 or 3.

Although exemplary embodiments of the invention have been shown and described, many changes, modifications and substitutions may be made by those having ordinary skill in the art without necessarily departing from the spirit and scope of this invention.

What is claimed is:

1. A method of vision correction comprising:

directing laser energy to a mask to provide a modulated laser beam having different energy levels at different locations across the modulated laser beam; and directing the modulated laser beam to a cornea of a patient to ablate a region of the cornea to different degrees to provide the cornea with progressive vision correction powers.

2. A method of vision correction as defined in claim 1 wherein the step of directing includes ablating first and second annular regions of the cornea to provide such annular regions with progressive vision correction powers, the progressive vision correction powers including progressive vision correction powers which increase in a radial direction across one of the first and second regions and decrease in said radial direction across the other of the first and second regions, said second region circumscribing the first region.

3. A method of vision correction comprising:

shaping first and second annular regions of the anterior surface of a cornea to provide a first anterior surface annular region with a first vision correction power and a second anterior surface annular region with a second vision correction power which is different from the first vision correction power to enhance vision at first and second different distances, respectively; and shaping a third annular region of the anterior surface of the cornea between said first and second anterior surface annular regions to provide a third anterior surface annular region with progressive vision correction powers which include progressive vision correction powers which are between the first and second vision correction powers, said second anterior surface annular region circumscribing the first anterior surface annular region.

4. A method of vision correction as defined in claim 3 including shaping a fourth annular region of the anterior surface of the cornea to provide a forth anterior surface annular region with progressive vision correction powers which include progressive vision correction powers which are between the first and second vision correction powers, said fourth anterior surface annular region circumscribing the second anterior surface annular region.

5. A method of vision correction as defined in claim 3 including shaping a central region of the anterior surface of the cornea to provide a vision correction power intermediate the first and second vision correction powers, said first anterior surface annular region circumscribing the central region.

6. A method of vision correction as defined in claim 3 wherein the cornea has an anterior surface and the first, second and third annular regions are located on the anterior surface.

7. A method of vision correction comprising shaping first, second and third regions of a cornea having an anterior surface to provide the first region located on the anterior surface with a first vision correction power and the second region located on the anterior surface with a second vision correction power which is different from the first vision correction power to enhance vision at first and second different distances, respectively, and the third region located between the first and second regions with progressive vision correction powers which include progressive vision correction powers which are between the first and second vision correction powers.

8. A method of vision correction as defined in claim 1 wherein the step of shaping is carried out to provide the first region with a near vision correction power and the second region with a far vision correction power.

9. A method of vision correction as defined in claim 7 wherein the step of shaping includes shaping a fourth region of the cornea to provide progressive vision correction powers which include progressive vision correction powers which are between the first and second vision correction powers, said second region being between the third region and the fourth region.

10. A method of vision correction as defined in claim 7 wherein the step of shaping includes directing laser energy to a mask which modulates the laser energy so the laser energy can shape the first and second regions of the cornea to provide the first and second vision correction powers.

11. A method of vision correction as defined in claim 7 including repeating said step of shaping said first and second regions of said cornea.

* * * * *